United States Patent
Okumura et al.

(10) Patent No.: US 6,447,118 B1
(45) Date of Patent: Sep. 10, 2002

(54) OPTICAL WATER-ABSORPTIVE GEL AND OPHTHALMIC MATERIAL USING THE SAME

(75) Inventors: Akiko Okumura, Kasugai; Kazuhiko Nakada, Nisshin, both of (JP)

(73) Assignee: Menicon Co., Ltd., Nagoya (JP)

( * ) Notice: Subject to any disclaimer, the term of this patent is extended or adjusted under 35 U.S.C. 154(b) by 0 days.

(21) Appl. No.: 09/569,198

(22) Filed: May 11, 2000

(30) Foreign Application Priority Data

May 21, 1999 (JP) .......................... 11-141479

(51) Int. Cl.$^7$ .................................. G02C 7/04
(52) U.S. Cl. .................................. 351/160 H
(58) Field of Search .................. 623/5.11, 6.11, 623/6.13, 6.56, 6.57, 6.6; 527/200; 526/266; 351/160 R, 160 H, 162, 213

(56) References Cited

U.S. PATENT DOCUMENTS

| 4,032,599 A | 6/1977 | Cordrey et al. |
| 4,268,132 A | 5/1981 | Neefe |
| 4,401,371 A | 8/1983 | Neefe |
| 5,858,077 A | 1/1999 | Kayanoki |

FOREIGN PATENT DOCUMENTS

| JP | 3-54519 | 3/1991 |
| JP | 6-347728 | 12/1994 |
| JP | 8-152582 | 6/1996 |
| JP | 11014949 | 1/1999 |
| WO | 83/02777 | 8/1983 |

Primary Examiner—George Manuel
(74) Attorney, Agent, or Firm—Burr & Brown

(57) ABSTRACT

An optical water-absorptive gel having a predetermined shape and consisting of a cross-linked water-absorptive polymer and an aqueous medium in which fine particles of a metal oxide are finely dispersed, the cross-linked water-absorptive polymer being swollen in the aqueous medium, so as to provide the predetermined shape in a gel state.

10 Claims, 1 Drawing Sheet

US 6,447,118 B1

OPTICAL WATER-ABSORPTIVE GEL AND OPHTHALMIC MATERIAL USING THE SAME

The present application is based on Japanese Patent Application No. 11-141479 filed May 21, 1999, the contents of which are incorporated hereinto by reference.

BACKGROUND OF THE INVENTION

1. Field of the Invention

The present invention relates in general to an optical water-absorptive gel and an ophthalmic material formed of the optical water-absorptive gel. In particular, the invention is concerned with the optical water-absorptive gel in which fine particles of a metal oxide are dispersed and which is capable of absorbing ultraviolet (UV) rays, and the ophthalmic material for a contact lens, an intraocular lens, an artificial cornea, etc.

2. Discussion of the Related Art

Water-absorptive gels (hydrogels) which are water-swollen with water held therein have been conventionally used for various applications. In the field of an ophthalmic material, for instance, a lens material for a contact lens or an intraocular lens, and an artificial cornea are advantageously formed of the water-absorptive gels, while utilizing characteristics of the water-absorptive gels.

An intraocular lens which is implanted in a patient's eye from which a crystalline lens has been removed in a cataract surgery, and a contact lens which is worn on a wearer's eye for rectifying the wearer's eyesight are preferably formed of a material capable of substantially preventing transmission therethrough of ultraviolet (UV) rays, like a natural crystalline of a human eye. In view of this, the lens material is generally formed of a water-absorptive gel to which a suitable UV absorbing agent such as benzotriazoles, benzophenones or derivatives of salicylic acid is added.

Metal oxides are used for various applications. In the field of the above-described lens material, for instance, titanium dioxide is used as a coloring material for producing a colored contact lens as disclosed in JP-A-3-54519. Described more specifically, the publication discloses a method of producing a colored contact lens by dispersing titanium dioxide as a coloring material in a suitable carrier, applying the obtained dispersed product or dispersion to a desired portion of a mold so as to imprint thereon a suitable pattern corresponding to an iris section of an intended lens, and polymerizing a monomer liquid introduced into the mold. The contact lens obtained according to the disclosed method has a colored iris section corresponding to the pattern imprinted on the above-indicated portion of the mold. JP-A-6-347782 and JP-A-8-152582 also disclose a method of producing a colored contact lens by first applying a coating of an ink including a coloring material such as iron oxide, chromium oxide or titanium oxide, to a surface portion of a base contact lens corresponding to its iris section, and then curing the ink, so that a colored layer which gives a colored iris section is formed on the above-indicated surface portion of the lens. All of the techniques disclosed in the above-indicated publications are intended to form the colored iris section in the contact lens, in other words, the obtained lens is used as an artificial eye or ocular prosthesis, wherein the colored iris section is opaque.

SUMMARY OF THE INVENTION

As a result of an extensive study about the water-absorptive gels made by the inventors of the present invention, the inventors have found a water-absorptive gel having a high degree of transparency sufficient for an optical use and capable of maintaining a desired shape, wherein a predetermined cross-linked water-absorptive polymer is swollen in an aqueous medium in which fine particles of a metal oxide are finely dispersed. In addition, it has been found that such water-absorptive gel can be advantageously used as an ophthalmic material exhibiting an excellent ultraviolet-ray-absorbing property.

It is therefore an object of the present invention to provide a novel optical water-absorptive gel exhibiting excellent characteristics. It is also an object of the invention to provide an ultraviolet-ray-absorbing ophthalmic material for a lens material or an artificial cornea, using the water-absorptive gel.

The objects of the present invention may be attained according to a principle of the invention, which provides an optical water-absorptive gel having a predetermined shape and consisting of a cross-linked water-absorptive polymer and an aqueous medium in which fine particles of a metal oxide are finely dispersed, the cross-linked water-absorptive polymer being swollen in the aqueous medium, so as to provide the predetermined shape in a gel state.

In the present optical water-absorptive gel, in spite of the inclusion of the metal oxide, the water-absorptive gel exhibits excellent optical characteristics having a sufficiently high degree of transparency, since the metal oxide is dispersed in the water-absorptive gel in the form of fine particles. The present water-absorptive gel wherein the fine particles of the metal oxide are dispersed exhibits excellent UV-ray-absorbing characteristics, so that the present water-absorptive gel can be advantageously used as an ophthalmic material such as a lens material for a contact lens or an intraocular lens, and an artificial cornea.

In a first preferred form of the present invention, the cross-linked water-absorptive polymer is formed by polymerizing at least one hydrophilic monomer and at least one cross-linkable monomer in the aqueous medium in which the fine particles of the metal oxide are finely dispersed. In the optical water-absorptive gel according to this arrangement, the predetermined cross-linked water-absorptive polymer is swollen in the aqueous medium such that the fine particles of the metal oxide are dispersed in the swollen polymer. The thus constructed water-absorptive gel has a predetermined shape.

In a second preferred form of the present invention, the fine particles of the metal oxide have a diameter of not greater than 25 nm. This arrangement permits the water-absorptive gel to have a sufficiently high degree of transparency.

In a third preferred form of the present invention, the metal oxide is selected from the group consisting of zinc oxide and titanium oxide.

In a fourth preferred form of the present invention, the metal oxide is dispersed in the aqueous medium in an amount of 0.3–5 wt.% of the cross-linked water-absorptive polymer. According to this arrangement, the water-absorptive gel exhibits excellent UV-ray-absorbing characteristics as well as a high degree of transparency.

In a fifth preferred form of the present invention, a ratio of the cross-linked water-absorptive polymer and the aqueous medium on a weight basis is held within a range of 90:10~20:80

In a sixth preferred form of the present invention, the at least one hydrophilic monomer is selected from the group consisting of hydroxyl group-containing (meth)acrylates, (meth)acrylamides and derivatives thereof, vinyl lactams, and (meth)acrylic acid.

The above-indicated objects of the present invention may also be attained according to another aspect of the present invention, which provides an ophthalmic material formed of the optical water-absorptive gel according to the above-described aspect of the invention, the optical water-absorptive gel absorbing UV rays. According to this arrangement, the optical water-absorptive gel is advantageously used as the ophthalmic material by making maximum use of the characteristics of the gel. The ophthalmic material comprises a lens material for a contact lens or an intraocular lens, and an artificial cornea.

BRIEF DESCRIPTION OF THE DRAWING

The above and optional objects, features and advantages of the present invention will be better understood by reading the following detailed description of a presently preferred embodiment of the invention when considered in conjunction with the accompanying drawing, in which the single figure is a graph showing a light transmission characteristic of the water-absorptive gel (in the form of a plate) of the specimen No. 1 in the Example described below.

DETAILED DESCRIPTION OF THE PREFERRED EMBODIMENT

Figure 1:
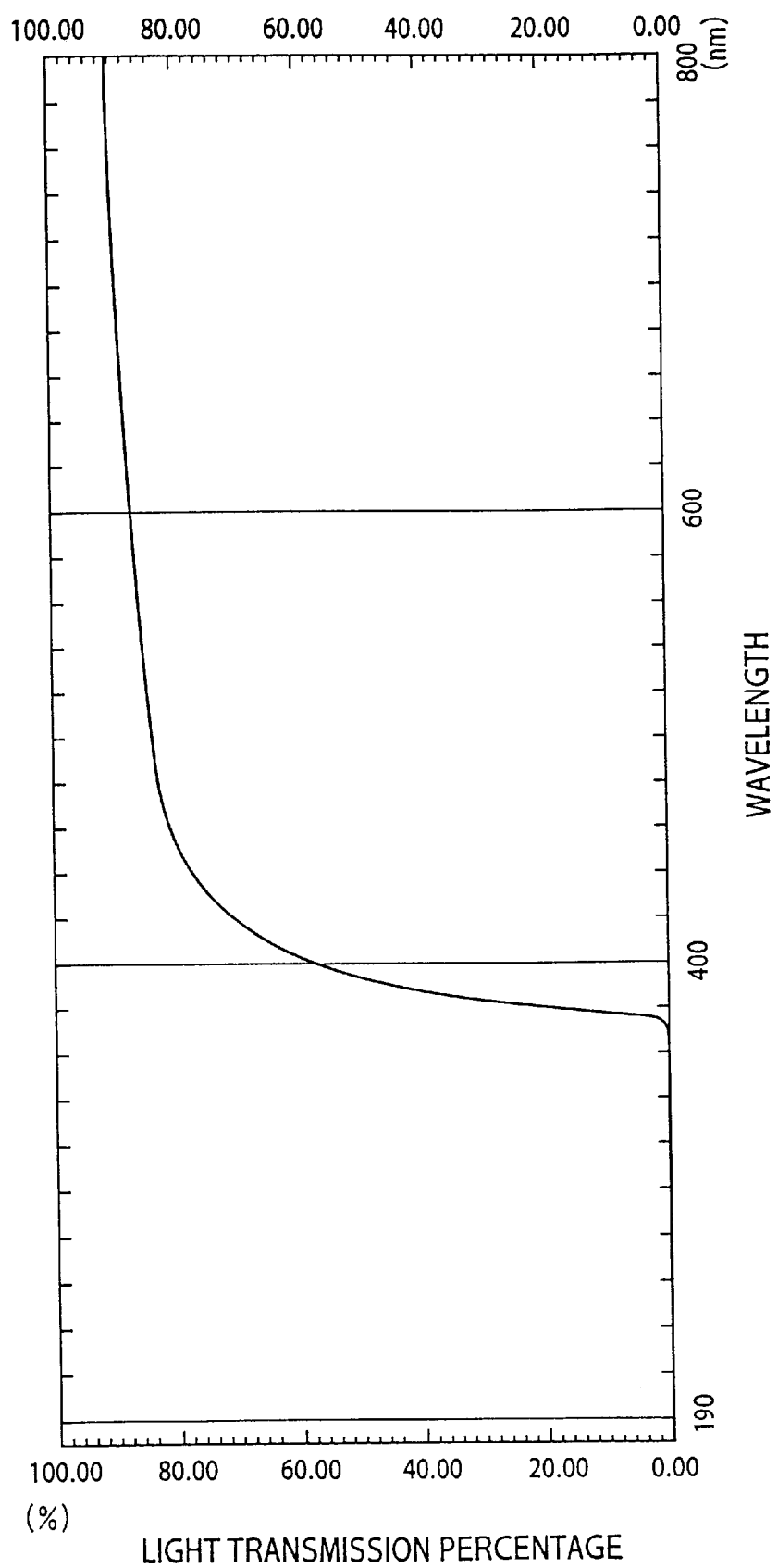

While the optical water-absorptive gel of the present invention can be obtained according to any methods, the present optical water-absorptive gel is advantageously obtained by first adding at least one hydrophilic monomer and at least one cross-linkable monomer which cooperate to give an intended cross-linked water-absorptive polymer, to an aqueous medium in which fine particles of a predetermined metal oxide are finely dispersed, and then polymerizing the hydrophilic monomer and the cross-linkable monomer in the aqueous medium, to thereby form the cross-linked water-absorptive polymer which is swollen in the aqueous medium and has a predetermined shape in a gel state, while the fine particles of the metal oxide are finely dispersed in the swollen polymer.

For imparting a high degree of transparency suitable for ophthalmic use (e.g., lens material or blank) to the optical water-absorptive gel of the present invention, the fine particles of the metal oxide dispersed in the gel preferably have a diameter of not greater than 25 nm, more preferably not greater than 15 nm for imparting a significantly high degree of transparency to the gel.

While any known metal oxides may be used, it is preferable in the present invention to employ zinc oxide or titanium oxide which can be easily produced into fine particles and which can be dispersed in the gel with high stability.

The metal oxide is included in the optical water-absorptive gel generally in an amount of 0.3–5 wt.% of the cross-linked water-absorptive polymer which gives the gel. If the amount of the metal oxide is too small, the obtained optical water-absorptive gel does not exhibit the desired UV-ray-absorbing property. If the amount of the metal oxide is excessively large, the transparency of the obtained water-absorptive gel is insufficient. For imparting an improved UV-ray-absorbing property and an improved degree of transparency to the water-absorptive gel, the metal oxide is included preferably in an amount of 0.5–3 wt.% of the cross-linked water-absorptive polymer.

The hydrophilic monomer and the cross-linkable monomer which are polymerized in the aqueous medium in which the fine particles of the metal oxide are finely dispersed are suitably selected from among known monomers which form a hydrogel used for the ophthalmic material such as the lens material for a contact lens or an intraocular lens, and an artificial cornea.

Examples of the hydrophilic monomer as a main component of the water-absorptive gel that gives such a hydrogel include: hydroxyl group-containing (meth)acrylates such as hydroxyetyl (meth)acrylate, hydroxypropyl (meth)acrylate, hydroxybutyl (meth)acrylate, dihydroxypropyl (meth)acrylate, dihydroxybutyl (meth)acrylate, diethylene glycol mono(meth)aylate. triethylene glycol mono(meth)acrylate, propylene glycol mono(meth)acrylate, and dipropylene glycol mono(meth)acrylate; (meth)acrylic acid; (meth)acrylamides and N-substituted derivatives thereof such as (meth)acrylamide, N-methyl (meth)acrylamide, N-ethyl (meth)acrylamide N,N-dimethyl (meth)acrylaride, NN-diethyl (meth)acrylamide, and N,N-methylethyl (meth)acrylanide. vinyl lactams such as N-vinyl pyrronolidone, N-vinyl piperidone, N-vinyl caprolactam, and N-vinyl capryllactam; aminoalkyl (meth)acrylates such as aminoethyl (meth)acrylate, N-methylaminoethyl (meth)acrylate, N,N-dimethylaminoetyl (meth)acrylate, and 2-butylaminoethyl (meth)acrylate; alkoxyl group-containing (meth)acrylates such as methoxyethyl (meth)acrylate, ethoxyethyl (meth)acrylate, methoxydiethylene glycol (meth)acrylate; maleic anhydride; maleic acid; fumarc acid; derivatives of fumaric acid; aminostyrene; and hydroxystyrene. Any one of, or any combination of these hydrophilic monomers are used.

Examples of the cross-linkable monomer which is polymerized together with the above-described hydrophilic monomer include: ethylene glycol di(meth)acrylate, diethylene glycol di(meth)acrylate, triethylene glycol di(meth)acrylate, propylene glycol di(meth)acrylate, dipropylene glycol di(meth)acrylate, diallyl fumarate, allyl (meth)acrylate, vinyl (meth)acrylate, trimethylolpropane tri(meth)acrylate, methacryloyloxyethyl (meth)acrylate, divinylbenzene, diallyl phthalate, diallyl adipate, triallyl diisocyanate, α-methylene-N-vinyl pyrrolidone, 4-vinylbenzyl (meth)acrylate, 3-vinylbenzyl (meth)acrylate, 2,2-bis[(meth)acryloyloxyphenyl]hexafluoropropane, 2,2-bis[(meth)acryloyloxyphenyl]propane, 1,4-bis[2-(meth)acryloyloxyhexafluoroisopropyl]benzene, 1,3-bis[2-(meth)acryloyloxyhexafluoroisopropyl]benzene, 1,2-bis[2-(meth)acryloyloxyhexafluoroisopropyl]benzene, 1,4-bis[2-(meth)acryloyloxyisopropyl]benzene, 1,3-bis[2-(meth)acryloyloxyisopropyl]benzene and 1,2-bis[2-(meth)acryloyloxyisopropyl]benzene. Any one of, or any combination of these cross-linkable monomers may be used.

In the above-described hydrophilic monomers and cross-linkable monomers, ". . . (meth)acrylate" is generic to the following two compounds: ". . . acrylate" and ". . . methacrylate".

The cross-linkable monomer is used for cross-linking a water-absorptive polymer which is formed by polymerization of the above-described hydrophilic monomer, and is present in the polymerization system of the hydrophilic monomer. The amount of the cross-linkable monomer to be used is preferably not less than 0.01 wt.%, more preferably not less than 0.05 wt.% of a total amount of the hydrophilic monomer and the cross-linkable monomer, so that the obtained cross-linked water-absorptive polymer, i.e., water-absorptive gel, has a significantly enhanced mechanical strength and durability. For avoiding adverse influences on the characteristics of the water-absorptive gel to be obtained, the upper limit of the amount of the cross-linkable monomer to be used is generally 10 wt.%, preferably 7 wt.% of the total amount of the hydrophilic monomer and the cross-linkable monomer.

The hydrophilic monomer and the cross-linkable monomer are added to the aqueous medium in an amount which is determined depending upon the required characteristics of the water-absorptive gel given by the cross-linked water-absorptive polymer which is formed by polymerization of the hydrophilic monomer and the cross-linkable monomer and which is swollen in the aqueous medium. In the present invention, the hydrophilic monomer and the cross-linkable monomer are added to the aqueous medium in an amount such that a ratio of the cross-linked water-absorptive polymer (which is formed by polymerization of the hydrophilic monomer and the cross-linkable monomer) and the aqueous medium on a weight basis is held within a range of 90:10~20:80.

The hydrophilic monomer and the cross-linkable monomer are added to the aqueous medium in which the fine particles of the predetermined metal oxide are finely dispersed, and polymerized according to any known methods. For instance, after a radical polymerization initiator is added to a mixture of the hydrophilic and cross-linkable monomers and the aqueous medium, the mixture is gradually heated from the room temperature to about 130° C. for polymerization. Alternatively, the hydrophilic monomer and the cross-linkable monomer in the aqueous medium are polymerized by exposure to an electromagnetic radiation such as a microwave, ultraviolet radiation, or radiant ray (γ-ray). The hydrophilic monomer and the cross-linkable monomer in the aqueous medium may be heat-polymerized with its temperature raised continuously or in steps.

Examples of the above-described radical polymerization initiator include azobisisobutyronitrile, azobisdimethylvaleronitrile, benzoyl peroxide, t-butyl hydroperoxide and cumene hydroperoxide. Any one of, or any combination of, these radical polymerization initiators may be used.

The hydrophilic monomer and the cross-linkable monomer in the aqueous medium may be photopolymerized. In this case, a suitable photopolymerization initiator or a photosensitizer is preferably used.

Any known photopolymerization initiator or photosensitizers may be used. Examples of the photopolymerization initiator include: benzoin photopolymerization initiators such as methylorthobenzoylbenzoate, methylbenzoylformate, benzoinmethylether, benzoinethylether, benzoinisopropylether, benzoinisobutylether, and benzoin-n-butylether; phenone photopolymerization initiators such as 2-hydroxy-2-methyl-1-phenylpropane-1-one, p-isopropyl-a-hydroxyisobutylphenone, p-t-butyltrichloroacetophenone, 2,2-dimethoxy-2-phenylacetophenone, α,α-dichloro-4-phenoxyacetophenone, and N,N-tetraethyl-4,4-diaminobenzophenone; 1-hydroxycyclohexylphenylketone; 1-phenyl-1,2-propanedione-2-(o-ethoxycarbonyl)oxime; thioxanthone photopolymerization initiators such as 2-chlorothioxanthone, and 2-methylthioxanthone; dibenzosuberone; 2-ethylanthraquinone; benzophenoneacrylate; benzophenone; and benzyl.

Thus, there is obtained the optical water-absorptive gel wherein the cross-linked water-absorptive polymer, which is formed by polymerization of the hydrophilic monomer and the cross-linkable monomer in the aqueous medium in which the fine particles of the metal oxide are finely dispersed, is swollen in the aqueous medium so as to form a gel while the fine particles of the metal oxide are dispersed in the swollen cross-linked water-absorptive polymer. The optical water-absorptive gel of the present invention is advantageously obtained by molding, so that the optical water-absorptive gel has a desired predetermined shape.

When the optical water-absorptive gel is produced by a molding method using a suitable mold, the mixture of the hydrophilic and cross-linkable monomers and the aqueous medium is introduced into a mold cavity of the mold whose profile follows that of a desired ophtalmic article such as a lens blank for a contact lens or an intraocular lens, and an artificial cornea. then hydrophilic and cross-linkable monomers are polymerized in the mold cavity, so as to provide a water-absorptive gel having a predetermined configuration, wherein the cross-linked water-absorptive polymer is swollen in the aqueous medium. The thus obtained water-absorptive gel is formed into the intended configuration by effecting thereon machining operations, as needed.

The optical water-absorptive gel may be produced by polymerization of the hydrophilic monomer and the cross-linkable monomer added to the aqueous medium, in an inner space of a suitable mold or a container, so as to provide a bar-shaped, block-shaped, or plate-shaped optical water-absorptive gel. The thus obtained optical water-absorptive gel is processed into a desired configuration suitable for ophthalmic use, by a known mechanical processing such as cutting or grinding.

The present optical water-absorptive gel obtained as described above is provided by the cross-linked water-absorptive polymer which is a copolymer of the hydrophilic monomer and the cross-linkable monomer and which is swollen in the aqueous medium in which the fine particles of the predetermined metal oxide are finely dispersed, and the optical water-absorptive gel has a predetermined shape in a gel state. The thus formed optical water-absorptive gel is transparent and capable of absorbing ultraviolet rays, so that the optical water-absorptive gel of the present invention can be used as the ophthalmic material such as the lens material for a contact lens or an intraocular lens, and an artificial cornea.

To further clarify the concept of the present invention, some examples of the invention will be described. It is to be understood that the invention is not limited to the details of the illustrated examples, but may be embodied with various changes, modifications and improvements, which may occur to those skilled in the art without departing from the scope of the invention defined in the attached claims.

EXAMPLE

Initially, there were prepared two kinds of dispersion liquids, wherein fine particles (having an average particle diameter of 5nm) of zinc oxide (ZnO) or titanium oxide ($TiO_2$) were finely dispersed in water. As the hydrophilic monomer, 2-hydroxyethyl methacrylate (HEMA) and N-vinylpyrrolidone (NVP) were prepared, while ethyleneglycol dimethacrylate (EDMA) was prepared as the cross-linkable monomer. As the photopolymerization initiator, 2-hydroxy-2-methyl-1-phenyl-1-propane-1-one (D1173) was prepared.

Next, to the dispersion liquids prepared as described above, there were added the hydrophilic monomers (HEMA, NVP), the cross-linkable monomer (EDMA), and the photopolymerization initiator (D1173) in respective amounts as indicated in the frollowing Table 1, so as to provide homogeneous polymeric mixtures. After the thus obtained polymeric mixtures were introduced into respective molds formed of polypropylene, the mixtures were photopolyineized by applying a UV radiation of 365 nm for 60 minutes on the upper side of the mixtures, using a black light of 1 mW/cm$^2$ ("FL10OBL-B" available from Matsushita Electronics Corporation, Japan). The thus obtained polymerized products were subjected to a hydration treatment, so that plate-shaped water-absorptive gels each having a thickness of 0.2 mm and a water content percentage as indicated in Table 1 were obtained. In each of the obtained water-absorptive gels, it was confirmed that the cross-linked water-absorptive polymer formed by the photopolymerization was swollen in the water, and that the fine particles of zinc oxide or titanium oxide were finely dispersed in the gel.

TABLE 1

| Components | Compositions (wt. %) | |
| --- | --- | --- |
| | No.1 | No.2 |
| EDMA | 0.1 | 0.1 |
| HEMA | 100 | 40 |
| NVP | — | 60 |
| water | 70 | 70 |
| D1173 | 0.2 | 0.2 |
| ZnO | 1.2 | — |
| TiO$_2$ | — | 2 |
| water content percentage (%) | 38 | 60 |

Each of the thus obtained two plate-shaped water-absorptive gels was measured of its light transmission percentage in a wavelength range which ranges from the wavelength of ultraviolet rays to that of a visible light, by irradiating each plate-shaped gel with a light having a wavelength of 190~800 nm, using an auto-recording spectrophotometer ("UV-3100" available from SHIMAZU SEISAKUSHO, CO., LTD, Japan). It was confirmed that each of the obtained gels substantially absorbed ultraviolet rays. The result of measurement of the light transmission percentage of the gel of the specimen No. 1 is shown in FIG. 1.

Assuming that the obtained water-absorptive gels are subjected to a disinfecting treatment when the gels are used as the ophthalmic material, it was inspected whether the gels were influenced by the disinfecting treatment. Described in detail, after the gels were heated in an autoclave at 121° C. for 20 minutes, the light transmission percentage was measured for each of the gels in a manner similar to that described above. It was confirmed that the light transmission percentage of the gels did not change after the disinfecting treatment, so that the water-absorptive gels exhibited the UV-ray-absorbing characteristics with high stability after the disinfecting treatment.

It was also confirmed that the obtained water-absorptive gels had a high degree of transparency suitable for use as the ophthalmic material such as a lens material for a contact lens or an intraocular lens, and an artificial cornea.

What is claimed is:

1. An optical water-absorptive gel having a predetermined shape and consisting of a cross-linked water-absorptive polymer and an aqueous medium in which fine particles of a metal oxide are finely dispersed, said cross-linked water-absorptive polymer being swollen in said aqueous medium, so as to provide said predetermined shape in a gel state.

2. An optical water-absorptive gel to claim 1, wherein said cross-linked water-absorptive polymer is formed by polymerizing at least one hydrophilic monomer and at least one cross-linkable monomer in said aqueous medium in which said fine particles of said metal oxide are finely dispersed.

3. An optical water-absorptive gel according to claim 1, wherein said fine particles of said metal oxide have a diameter of not greater than 25 nm.

4. An optical water-absorptive gel according to claim 1, wherein said metal oxide is selected from the group consisting of zinc oxide and titanium oxide.

5. An optical water-absorptive gel according to claim 1, wherein said metal oxide is dispersed in said aqueous-medium in an amount of 0.3-5 wt.% of said cross-linked water-absorptive polymer.

6. An optical water-absorptive gel according to claim 1, wherein a ratio of said cross-linked water-absorptive polymer and said aqueous medium on a weight basis is held within a range of 90:10~20:80.

7. An optical water-absorptive gel according to claim 1, wherein said at least one hydrophilic monomer is selected from the group consisting of hydroxyl group-containing (meth) acrylates, (meth) acrylamides and derivatives thereof, vinyl lactams, and (meth) acrylic acid.

8. An ophthalmic material formed of said optical water-absorptive gel as defined in claim 1, said optical water-absorptive gel absorbing UV rays.

9. An ophthalmic material according to claim 8, comprising a lens material for a contact lens and an intraocular lens.

10. An ophthalmic material according to claim 8, comprising an artificial cornea.

* * * * *